(12) United States Patent
Lee et al.

(10) Patent No.: US 10,266,817 B2
(45) Date of Patent: Apr. 23, 2019

(54) BOTULINUM TOXIN-HUMAN EPIDERMAL GROWTH FACTOR FUSION PROTEIN WITH INCREASED SKIN CELL PROLIFERATION AND ANTI-OXIDATION EFFECT AND COSMETIC COMPOSITION FOR REGENERATING SKIN AND IMPROVING SKIN WRINKLE COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Han Bong Ryu, Seoul (KR); Seong Ran Lee, Gyeonggi-do (KR); Jong Nam Choi, Gyeonggi-do (KR); Tae Won Choi, Seoul (KR); Tae Hyun Kim, Gyeonggi-do (KR); Tae Hwa Jeong, Gyeonggi-do (KR); Hyeong Il Kwon, Seoul (KR)

(73) Assignees: NEXGEN BIOTECHNOLOGIES, INC., Seoul (KR); Sun Kyo Lee, Gyeonggi-do (KR)

( * ) Notice: Subject to any disclaimer, the term of this patent is extended or adjusted under 35 U.S.C. 154(b) by 0 days.

(21) Appl. No.: 15/522,160

(22) PCT Filed: Jul. 22, 2016

(86) PCT No.: PCT/KR2016/007985
§ 371 (c)(1),
(2) Date: Apr. 26, 2017

(87) PCT Pub. No.: WO2017/213287
PCT Pub. Date: Dec. 14, 2017

(65) Prior Publication Data
US 2019/0093095 A1 Mar. 28, 2019

(30) Foreign Application Priority Data

Jun. 8, 2016 (KR) ........................ 10-2016-0071284

(51) Int. Cl.
| | |
|---|---|
| *C12N 9/52* | (2006.01) |
| *C07K 14/485* | (2006.01) |
| *C12N 15/62* | (2006.01) |
| *A61K 8/66* | (2006.01) |
| *A61Q 19/00* | (2006.01) |
| *A61Q 19/08* | (2006.01) |
| *C12N 15/70* | (2006.01) |

(52) U.S. Cl.
CPC .............. *C12N 9/52* (2013.01); *A61K 8/66* (2013.01); *A61Q 19/00* (2013.01); *A61Q 19/08* (2013.01); *C07K 14/485* (2013.01); *C12N 15/62* (2013.01); *C12N 15/70* (2013.01); *C12Y 304/24069* (2013.01); *C07K 2319/55* (2013.01)

(58) Field of Classification Search
None
See application file for complete search history.

(56) References Cited

FOREIGN PATENT DOCUMENTS

| | | |
|---|---|---|
| JP | 2006-519761 A | 8/2006 |
| KR | 10-2005-0027838 A | 3/2005 |
| KR | 10-2012-0061618 A | 6/2012 |
| KR | 10-2015-0056022 A | 5/2015 |
| KR | 10-2015-0144735 A | 12/2015 |
| WO | WO 2015/063613 A2 | 5/2015 |

OTHER PUBLICATIONS

Hanahan, Douglas, "Studies on Transformation of *Escherichia coli* with Plasmids", J. Mol. Biol. vol. 166, pp. 557-580, 1983.
Fahrer, Jorg et al., "A Cell-Permeable Fusion Protein Based on Clostridium botulinum C2 Toxin for Delivery of p53 Tumorsuppressor into Cancer Cells", PLOS One, vol. 8, Issue 9, e72455, pp. 1-9, Sep. 2013.
Yang, Xiaoping et al.,"Diphtheria Toxin—Epidermal Growth Factor Fusion Protein DAB389EGF for the Treatment of Bladder Cancer", Cancer Therapy: Preclinical, Clinical Cancer Research, vol. 19, No. 1, pp. 148-157, 2013.
Chandramohan, Vidyalakshmi et al., "Toxin-Based Targeted Therapy for Malignant Brain Tumors", Clinical and Developmental Immunology, vol. 2012, Article ID 480429, Internal pp. 1-15, 2012.
Thakur, Mayank et al., "Targeted tumor therapy by epidermal growth factor appended toxin and purified saponin: An evaluation of toxicity and therapeutic potential in syngeneic tumor bearing mice", Molecular Oncology, vol. 7, pp. 475-483, 2013.
NCBI, GenBank, "neurotoxin A [Clostridium botulinum]", Access on No. ABM73969.1, Feb. 2007.

*Primary Examiner* — Sarvamangala Devi
(74) *Attorney, Agent, or Firm* — The PL Law Group, PLLC

(57) ABSTRACT

A botulinum toxin-human epidermal growth factor fusion protein with increased skin cell proliferation and anti-oxidation effect has the amino acid sequence of SEQ ID NO: 2, a gene consisting of *E. coli* (*Escherichia coli*) codon-optimized nucleotide sequence of SEQ ID NO: 1 for encoding the botulinum toxin-human epidermal growth factor fusion protein, a recombinant vector including the gene, a host cell transformed with the recombinant vector, and a method for producing a botulinum toxin-human epidermal growth factor fusion protein by transforming a host cell with the recombinant vector, and a cosmetic composition for regenerating skin and improving skin wrinkle including, as an effective component, a botulinum toxin-human epidermal growth factor fusion protein, and as the cosmetic composition has an effect of regenerating skin and improving skin wrinkle, it can be advantageously used in future in the field of cosmetics or cosmetic plastic surgery.

14 Claims, 4 Drawing Sheets
Specification includes a Sequence Listing.

SEQUENCE LISTING

<160> NUMBER OF SEQ ID NOS: 6

<210> SEQ ID NO 1
<211> LENGTH: 1503
<212> TYPE: DNA
<213> ORGANISM: Artificial Sequence
<220> FEATURE:
<223> OTHER INFORMATION: BTAL-EGF

<400> SEQUENCE: 1

| | | | | |
|---|---|---|---|---|
| atgccgttcg ttaacaaaca gttcaactac aaagacccgg ttaacggtgt tgacatcgcg | 60 |
| tacatcaaaa tcccgaacgt tggtcagatg cagccggtta aagcgttcaa aatccacaac | 120 |
| aaaatctggg ttatcccgga acgtgacacc ttcaccaacc cggaagaagg tgacctgaac | 180 |
| ccgccgccgg aagcgaaaca ggttccggtt tcttactacg actctaccta cctgtctacc | 240 |
| gacaacgaaa aagacaacta cctgaaaggt gttaccaaac tgttcgaacg tatctactct | 300 |
| accgacctgg gtcgtatgct gctgacctct atcgttcgtg gtatcccgtt ctggggtggt | 360 |
| tctaccatcg acaccgaact gaaagttatc gacaccaact gcatcaacgt tatccagccg | 420 |
| gacggttctt accgttctga agaactgaac ctggttatca tcggtccgtc tgcggacatc | 480 |
| atccagttcg aatgcaaatc tttcggtcac gaagttctga acctgacccg taacggttac | 540 |
| ggttctaccc agtacatccg tttctctccg gacttcacct tcggtttcga agaatctctg | 600 |
| gaagttgaca ccaacccgct gctgggtgcg gtaaattcg gaccgaccc ggcggttacc | 660 |
| ctggcgcacg aactgatcca cgcgggtcac cgtctgtacg gtatcgcgat caaccccgaac | 720 |
| cgtgttttca agttaacac caacgcgtac tacgaaatgt ctggtctgga gtttctttc | 780 |
| gaagaactgc gtaccttcgg tggtcacgac gcgaaattca tcgactctct gcaggaaaac | 840 |
| gaattccgtc tgtactacta acaaaattc aaagacatcg cgtctaccct gaacaaagcg | 900 |
| aaatctatcg ttggtaccac cgcgtctctg cagtacatga aaacgttttt caaagaaaaa | 960 |
| tacctgctgt ctgaagacac ctctggtaaa ttctctgttg acaaactgaa attcgacaaa | 1020 |
| ctgtacaaaa tgctgaccga aatctacacc gaagacaact tcgttaaatt cttcaaagtt | 1080 |
| ctgaaccgta aacctacct gaacttcgac aaagcggttt tcaaaatcaa catcgttccg | 1140 |
| aaagttaact acaccatcta cgacggtttc aacctgcgta caccaacct ggcggcgaac | 1200 |
| ttcaacggtc agaacaccga atcaacaac atgaacttca ccaaactgaa aaacttcacc | 1260 |
| ggtctgttcg aattctacaa actgctgtgc gttcgtggta tcatcacctc taaaaccaaa | 1320 |
| tctctggaca aaggttacaa caaaaactca gactctgagt gcccactgtc tcacgacggc | 1380 |
| tactgccttc acgacggagt ctgcatgtac atcgaggctt tggataagta cgcttgtaat | 1440 |
| tgcgtcgttg gttacattgg agagcgctgc caataccgtg acttaaaatg gtgggagttg | 1500 |
| cgc | 1503 |

<210> SEQ ID NO 2
<211> LENGTH: 501
<212> TYPE: PRT
<213> ORGANISM: Artificial Sequence
<220> FEATURE:
<223> OTHER INFORMATION: BTAL-EGF

<400> SEQUENCE: 2

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro

-continued

```
Val Lys Ala Phe Lys Ile His Asn Lys Ile Trp Val Ile Pro Glu Arg
         35                  40                  45
Asp Thr Phe Thr Asn Pro Glu Glu Gly Asp Leu Asn Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
             100                 105                 110
Arg Gly Ile Pro Phe Trp Gly Gly Ser Thr Ile Asp Thr Glu Leu Lys
         115                 120                 125
Val Ile Asp Thr Asn Cys Ile Asn Val Ile Gln Pro Asp Gly Ser Tyr
 130                 135                 140
Arg Ser Glu Glu Leu Asn Leu Val Ile Ile Gly Pro Ser Ala Asp Ile
 145                 150                 155                 160
Ile Gln Phe Glu Cys Lys Ser Phe Gly His Glu Val Leu Asn Leu Thr
                 165                 170                 175
Arg Asn Gly Tyr Gly Ser Thr Gln Tyr Ile Arg Phe Ser Pro Asp Phe
             180                 185                 190
Thr Phe Gly Phe Glu Glu Ser Leu Glu Val Asp Thr Asn Pro Leu Leu
         195                 200                 205
Gly Ala Gly Lys Phe Ala Thr Asp Pro Ala Val Thr Leu Ala His Glu
 210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                 245                 250                 255
Glu Val Ser Phe Glu Glu Leu Arg Thr Phe Gly Gly His Asp Ala Lys
             260                 265                 270
Phe Ile Asp Ser Leu Gln Glu Asn Glu Phe Arg Leu Tyr Tyr Tyr Asn
         275                 280                 285
Lys Phe Lys Asp Ile Ala Ser Thr Leu Asn Lys Ala Lys Ser Ile Val
 290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                 325                 330                 335
Lys Phe Asp Lys Leu Tyr Lys Met Leu Thr Glu Ile Tyr Thr Glu Asp
             340                 345                 350
Asn Phe Val Lys Phe Phe Lys Val Leu Asn Arg Lys Thr Tyr Leu Asn
         355                 360                 365
Phe Asp Lys Ala Val Phe Lys Ile Asn Ile Val Pro Lys Val Asn Tyr
 370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                 405                 410                 415
Lys Asn Phe Thr Gly Leu Phe Glu Phe Tyr Lys Leu Leu Cys Val Arg
             420                 425                 430
Gly Ile Ile Thr Ser Lys Thr Lys Ser Leu Asp Lys Gly Tyr Asn Lys
         435                 440                 445
```

```
Asn Ser Asp Ser Glu Cys Pro Leu Ser His Asp Gly Tyr Cys Leu His
    450             455             460
Asp Gly Val Cys Met Tyr Ile Glu Ala Leu Asp Lys Tyr Ala Cys Asn
465             470             475             480
Cys Val Val Gly Tyr Ile Gly Glu Arg Cys Gln Tyr Arg Asp Leu Lys
                485             490             495
Trp Trp Glu Leu Arg
            500

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
aaggagatat acatatgccg ttcgttaac                              29

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gtctgagttt ttgttgtaac                                        20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gttacaacaa aaactcagac                                        20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtgctcgagg cgcaactccc                                        20
```

BOTULINUM TOXIN-HUMAN EPIDERMAL GROWTH FACTOR FUSION PROTEIN WITH INCREASED SKIN CELL PROLIFERATION AND ANTI-OXIDATION EFFECT AND COSMETIC COMPOSITION FOR REGENERATING SKIN AND IMPROVING SKIN WRINKLE COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/007985, filed Jul. 22, 2016, which claims priority to the benefit of Korean Patent Application No. 10-2016-0071284 filed in the Korean Intellectual Property Office on Jun. 8, 2016, the entire contents of which are incorporated herein by reference.

TECHNICAL FIELD

The present invention relates to a botulinum toxin-human epidermal growth factor fusion protein with increased skin cell proliferation and anti-oxidation effect and a cosmetic composition for regenerating skin and improving skin wrinkle comprising the same as effective component.

BACKGROUND ART

The modern day cosmetic industry focuses on development and application of new materials as raw materials for cosmetics are being depleted. Currently, development of techniques for having new materials and development of cosmetics with high performance are continuously made in the entire cosmetic industry. In particular, the human epidermal growth factor (hEGF) is one of the materials which draw attention of consumers as it has an excellent skin regeneration effect like wrinkle improvement and whitening.

After arriving at adulthood (i.e., around 25 years old), human skin experiences an occurrence of pigmentation, wrinkle, or the like and a progress of skin aging phenomenon as body metabolism or cellular regeneration activity is slowed down. The human epidermal growth factor with excellent skin regeneration effect has been used as a medicinal therapeutic agent for skin regeneration. However, studies are mainly made on use of the human epidermal growth factor as a raw material of functional cosmetics for aging prevention which has an activity of recovering lowered skin regeneration activity and promoting new skin cell growth.

Upon binding to a receptor for an epidermal growth factor present on a surface of a cell, the human epidermal growth factor (hEGF) induces a dimerization of a receptor for an epidermal growth factor. A dimeric receptor for an epidermal growth factor activates the tyrosine kinase present in the receptor to induce an intracellular signal transduction system. As a result of those processes, glycolysis and protein synthesis are promoted in a cell, eventually leading to cell growth.

The epidermal growth factor playing an important role in skin regeneration decreases according to a progress of aging, and a decrease in the epidermal growth factor causes a reduction in skin cell proliferation and transfer, and thus phenomena like skin aging, increased winkles, and reduced skin elasticity are exhibited accordingly.

Botulinum toxin which has been first found from *Clostridium botulinum* was initially used for medical purpose based on its effect of anesthetizing a motor neuron. In particular, when an extremely amount of botulinum toxin is selectively used for a limited area, it was shown that symptoms related to muscular or neuronal disorder can be treated. Accordingly, Allergan Inc., which is a US pharmaceutical company, provides a commercial product of low-concentration botulinum toxin A in the trade name of Botox. In South Korea, total 4 kinds of botulinum toxin are commercially available, i.e., Botox, Botulex (South Korea), Meditoxin (South Korea), Dysport (Europe), and BTXA (China). Since 1990s, Botox has been known to have an effect of removing skin wrinkle, and thus it is now used all over the world for the purpose of removing skin wrinkle in the field of cosmetic surgery.

In year 2002, Botox has been approved by U.S. Food and Drug Administration (FDA) as an agent for treating curved lines between eyebrows, and its popularity as a cosmetic treatment agent continues until now. For botulinum toxin which is most popular as a therapeutic agent for improving skin wrinkle in cosmetic industry, an injection treatment is used. However, the biggest disadvantage lies in that the treatment effect prolongs only for 3 to 6 months and it is quite expensive.

In the present invention, to have more effectively prolonged activity of botulinum toxin which has an excellent skin removing effect in the field of cosmetic plastic surgery, development of a new protein to have distinct skin regeneration effect was carried out, in particular. As a result, it was confirmed that a new fusion protein with dual function, which is produced according to binding of a human epidermal growth factor with excellent skin regeneration effect, has maximized skin improvement and accelerated skin regeneration effect.

Meanwhile, in Korean Patent Application Publication No. 2015-0144735, a "composition comprising filler and botulinum toxin for improving skin wrinkle or skin aging, or treating neuromuscular disorder" is disclosed. Furthermore, in Korean Patent Application Publication No. 2015-0056022, a "cosmetic composition for improving skin comprising fusion protein of epidermal grown factor" is disclosed. However, no description has been made for the botulinum toxin-human epidermal growth factor fusion protein with increased skin cell proliferation and anti-oxidation effect and a cosmetic composition for regenerating skin and improving skin wrinkle comprising the same as effective component of the present invention.

SUMMARY

The present invention is devised in view of the circumstances described above, and according to fusion of human epidermal growth factor to a botulinum toxin protein, the inventors of the present invention produced a novel botulinum toxin-human epidermal growth factor fusion protein with increased cell proliferation and anti-oxidation effect. The botulinum toxin-human epidermal growth factor fusion protein was confirmed to have more excellent skin cell proliferation and anti-oxidation effect than human epidermal growth factor, and the present invention is completed accordingly.

To solve the problems described above, the present invention provides a botulinum toxin-human epidermal growth factor fusion protein with increased skin cell proliferation and anti-oxidation effect which consists of the amino acid sequence of SEQ ID NO: 2.

The present invention also provides a gene encoding the aforementioned fusion protein.

The present invention also provides a recombinant vector comprising the aforementioned gene.

The present invention also provides a host cell transformed with the aforementioned recombinant vector.

The present invention also provides a method for producing in a host cell a botulinum toxin-human epidermal growth factor fusion protein comprising overexpressing a gene encoding a botulinum toxin-human epidermal growth factor fusion protein by transforming a host cell with the aforementioned recombinant vector.

The present invention also provides a botulinum toxin-human epidermal growth factor fusion protein which is prepared by the aforementioned method.

The resent invention also provides a cosmetic composition for regenerating skin and improving skin wrinkle comprising, as an effective component, a botulinum toxin-human epidermal growth factor fusion protein which consists of the amino acid sequence of SEQ ID NO: 2.

The method of production in *E. coli* using *E. coli* codon-optimized gene encoding botulinum toxin-human epidermal growth factor fusion protein of the present invention has a simplified production step as proteins are expressed in the form of an inclusion body in *E. coli* (*Escherichia coli*) and allows large scale production of proteins Furthermore, as the botulinum toxin-human epidermal growth factor fusion protein produced by the aforementioned method has an excellent function of regenerating skin and improving skin wrinkle, it is expected that the fusion protein is advantageously used as a raw material of functional cosmetics.

DETAILED DESCRIPTION

Figure 1:
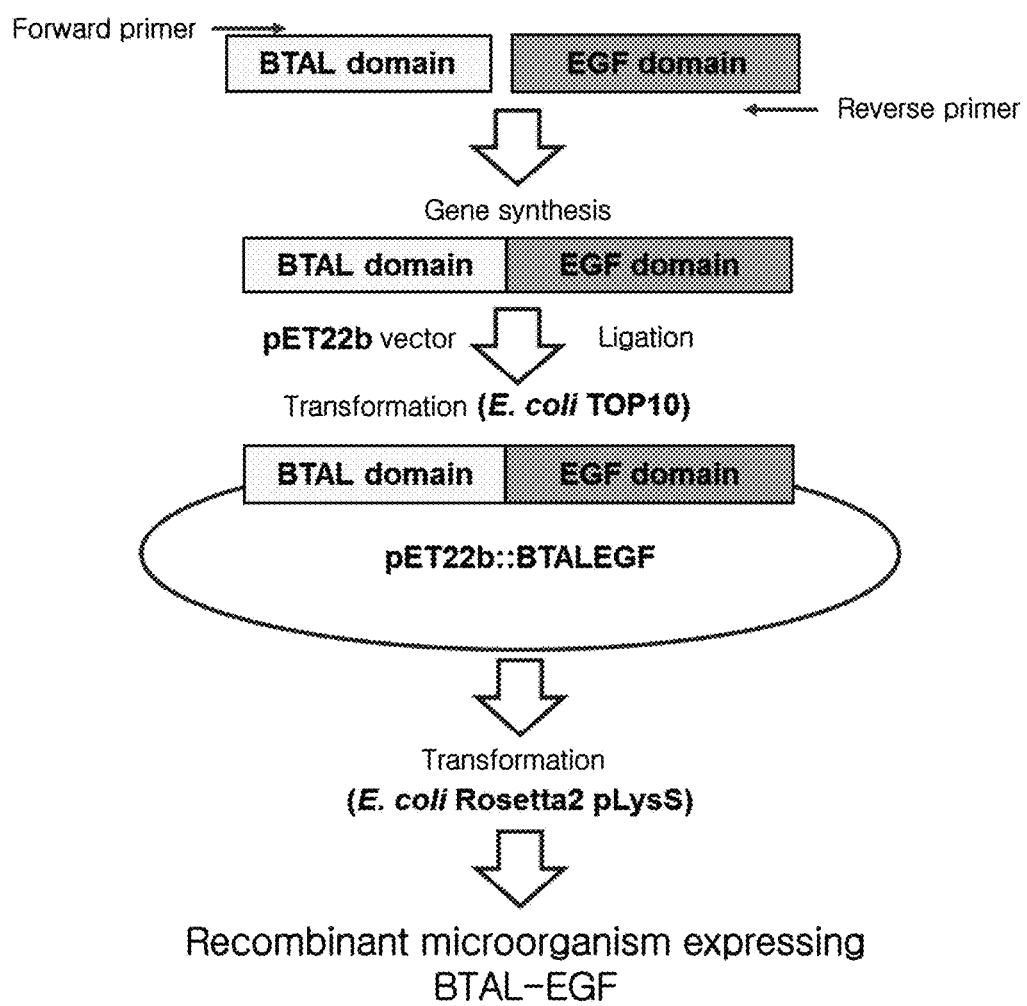
FIG. 1 is a schematic drawing illustrating the process for preparing the recombinant plasmid (pET22b::BTALEGF) which includes a gene encoding the botulinum toxin-human epidermal growth factor fusion protein, and transforming *E. coli* with the plasmid.

To achieve the object of the present invention, the present invention provides a botulinum toxin-human epidermal growth factor fusion protein with increased cell proliferation and anti-oxidation effect which consists of the amino acid sequence of SEQ ID NO: 2.

The scope of the botulinum toxin-human epidermal growth factor fusion protein according to the present invention includes a protein having an amino acid sequence represented by SEQ ID NO: 2, and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein exhibiting substantially the same physiological activity as the protein represented by SEQ ID NO: 2. The expression "substantially the same physiological activity" means an activity of regenerating skin and improving skin wrinkle. Furthermore, included in the botulinum toxin-human epidermal growth factor fusion protein are a fragment, a derivative, and an analogue thereof. The terms "fragment", "derivative", and "analogue" that are used herein indicate a polypeptide which has substantially the same physiological function or activity as the botulinum toxin-human epidermal growth factor fusion protein of the present invention.

The botulinum toxin-human epidermal growth factor fusion protein of the present invention preferably consists of SEQ ID NO: 2, and it may be a novel protein which is produced by fusion between the botulinum toxin protein consisting of the $1^{st}$ to the $448^{th}$ amino acids and the human epidermal growth factor protein consisting of the $449^{th}$ to the $501^{st}$ amino acids of the above amino acid sequence.

The present invention further provides a gene encoding the botulinum toxin-human epidermal growth factor fusion protein with increased skin cell proliferation and anti-oxidation effect. This gene may consist of a nucleotide sequence of *E. coli* codon-optimized SEQ ID NO: 1, but not limited thereto.

The gene encoding the botulinum toxin-human epidermal growth factor fusion protein with increased skin proliferation and anti-oxidation effect of the present invention may include a nucleotide sequence of SEQ ID NO: 1. Further, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon optimization" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1 of the present invention is a sequence which has been optimized to *E. coli* codon such that the gene encoding the botulinum toxin-human epidermal growth factor fusion protein can be expressed well in *E. coli*.

The present invention also provides a recombinant vector comprising the gene described above, and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding human botulinum toxin-human epidermal growth factor fusion protein can be inserted to a recombinant expression vector. The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising the gene sequence encoding the botulinum toxin-human epidermal growth factor fusion protein and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of 5' terminal (NdeI restriction enzyme site) and 3' terminal (XhoI restriction enzyme site) of the gene encoding the botulinum toxin-human epidermal growth factor fusion protein (SEQ ID NO: 1) to pET22b vector, and it is a vector characterized in that it can produce the botulinum toxin-human epidermal growth factor fusion protein based on effective expression of the aforementioned gene with an aid of lac promoter (lac promoter) and lad repressor (lad repressor).

For a host cell having an ability of having stable and continuous cloning and expression of the vector of the present invention, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyce cerevisiae*), an insect cell, a human cell (for example, CHO (Chinese hamster ovary) cell line, W138, BHK, COS-7, 293, HepG2, 3T3, RIN, and MDCK cell line), a plant cell, and the like can be used as a host cell.

The host cell transformed with the recombinant vector according to one embodiment of the present invention can be *E. coli* Rosetta2 (DE3) pLysS, but not limited thereto.

When a host cell is a prokaryotic cell, delivery of the recombinant vector of the present invention into a host cell can be carried out by $CaCl_2$ method, Hanahan's method (Hanahan, D., J. Mol. Biol., 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a botulinum toxin-human epidermal growth factor fusion protein comprising overexpressing a gene encoding a botulinum toxin-human epidermal growth factor fusion protein by transforming a host cell with the recombinant vector described above.

With regard to the method according to one embodiment of the present invention, the host cell can be preferably *E. coli*, and more preferably *E. coli* Rosetta2 (DE3) pLysS, but not limited thereto.

The present invention further provides a botulinum toxin-human epidermal growth factor fusion protein which is prepared by the aforementioned method.

The present invention still further provides a cosmetic composition for regenerating skin and improving skin wrinkle comprising, as an effective component, a botulinum toxin-human epidermal growth factor fusion protein which consists of the amino acid sequence of SEQ ID NO: 2.

In the cosmetic composition according to one embodiment of the present invention, content of the botulinum toxin-human epidermal growth factor fusion protein may be 0.000002 to 0.02% by weight relative to the total weight of the cosmetic composition, but not limited thereto.

In the cosmetic composition of the present invention, components that are typically used for a cosmetic composition are included in addition to the effective components that are described above. Examples thereof include a lipid material, an organic solvent, a dissolution agent, a condensation agent, a gelling agent, a softening agent, an antioxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or liphophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder. In particular, in a case in which the cosmetic composition is a spray, a propellant such as chlorofluorohydrocarbon, propane/butane, or dimethyl ether may be additionally included.

In a case in which the cosmetic composition of the present invention has a formulation type of solution or emulsion, a solvent, a dissolution agent, or an emulsifier is used as a carrier component, and examples thereof include isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Expression Vector and Transformed Recombinant Microorganism for Producing Botulinum Toxin-Human Epidermal Growth Factor Fusion Protein The optimized gene encoding the botulinum toxin-human epidermal growth factor fusion protein, recombinant expression vector, and transformed recombinant microorganism were prepared in accordance with the following methods.

By using as a template the genes encoding the botulinum toxin (hereinbelow, BTAL) protein or human epidermal growth factor (hereinbelow, hEGF) used as a partner protein, the gene (SEQ ID NO: 1) fragment encoding the botulinum toxin-human epidermal growth factor fusion protein which consists of 501 amino acids and has been optimized for expression in a host microorganism was prepared and synthesized.

To synthesize the gene encoding the botulinum toxin-human epidermal growth factor fusion protein (SEQ ID NO: 2) having the human epidermal growth factor bound to the carboxy terminal (C-terminal) of botulinum toxin, 1344 bp nucleotide (i.e., $1^{st}$ to $1344^{th}$ nucleotides of SEQ ID NO: 1) encoding the botulinum toxin, which has been optimized for E. coli, was synthesized by using a forward primer 1 (5'-AAGGAGATATA<u>CATATG</u>CCGTTCGTTAAC-3', SEQ ID NO: 3) and a reverse primer 1 (5'-GTCTGAGTTTTT-GTTGTAAC-3', SEQ ID NO: 4). Furthermore, 159 bp nucleotide (i.e., $1345^{th}$ to $1503^{rd}$ nucleotides of SEQ ID NO: 1) encoding the human epidermal growth factor, which has been optimized for E. coli, was synthesized by using a forward primer 2 (5'-GTTACAACAAAAACTCAGAC-3', SEQ ID NO: 5) and a reverse primer 2 (5'-GTG <u>CTCGAG</u>GCGCAACTCCC-3', SEQ ID NO: 6). By having each of the genes encoding botulinum toxin protein or the human epidermal growth factor, which have been synthesized by the above method, as a template and also by using a forward primer 1 (SEQ ID NO: 3) and a reverse primer 2 (SEQ ID NO: 6), a gene consisting of 1503 nucleotides encoding a fusion protein in which human epidermal growth factor is bound to the C-terminal of the botulinum toxin was finally obtained by polymerase chain reaction (PCR).

The aforementioned gene fragment and recombinant plasmid were digested with the same restriction enzymes (5' terminal NdeI and 3' terminal XhoI) followed by insertion, and thus the recombinant plasmid (pET22b::BTALEGF) shown in FIG. 1 was prepared. Then, E. coli TOP10 was transformed with the prepared recombinant plasmid to obtain a large amount of the gene construct from the host microorganism.

After that, E. coli Rosetta2 (DE3) pLysS (Novagen, Germany) was transformed with the prepared recombinant plasmid to produce a recombinant microorganism for producing a botulinum toxin-human epidermal growth factor fusion protein.

Example 2. Expression Induction, Isolation, and Purification of Botulinum Toxin-Human Epidermal Growth Factor Fusion Protein E. coli Rosetta2 (DE3) pLysS prepared in Example 1 was cultured in 1 L LB medium (10% tryptophan, 10% sodium chloride, and 5% yeast extract) or BSB medium (1% tryptophan, 0.5% yeast extract, 1% glucose, and 0.1% HEPES (pH 7.0), manufactured by Nexgen Biotechnologies, Inc.) till to have $OD_{600}$=0.6 to 0.8 for batch culture, or $OD_{600}$=15 to 20 for continuous culture using 20 L fermentation apparatus. After that, by adding 1 to 5 mM IPTG or 2% lactose (both in final concentration) to each cell culture medium, expression of recombinant E. coli was induced. After gene expression induction, the cells were further cultured for 3 to 4 hours, and then collected by centrifuge. The collected cells were sufficiently suspended in a buffer solution (phosphate buffered saline, 8 g of sodium chloride, 0.2 g of potassium chloride, 1.44 g of sodium hydrogen phosphate ($Na_2HPO_4$), and 0.24 g of potassium dihydrogen phohsphate ($KH_2PO_4$)/l, pH 7.4) and disrupted using an ultrasonic cell homogenizer. As a result, a solution containing intracellular proteins was separated.

Figure 2A:
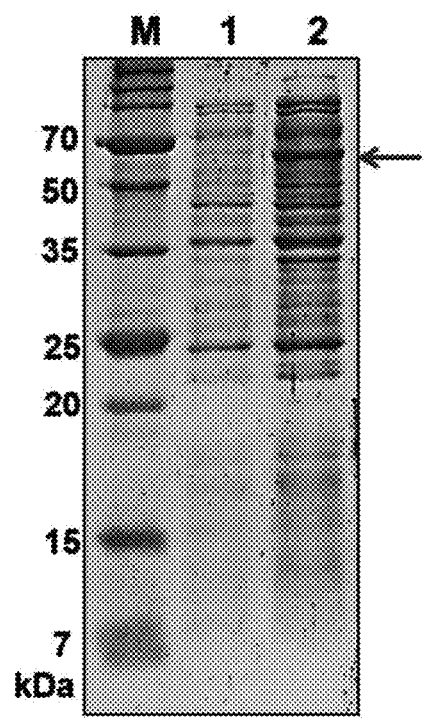
FIGS. 2A and 2B show the results of determining the expression of the botulinum toxin-human epidermal growth factor fusion protein in *E. coli* by SDS-polyacrylamide gel electrophoresis (FIG. 2A), and the result of determining the EGF domain by using an EGF detection kit to see the presence or absence of a human epidermal growth factor in the fusion protein (FIG. 2B). M; size marker, 1; crude cell lysate before expression induction, 2; crude cell lysate after expression induction, C; EGF control group, and T; test sample (fusion protein).

By using the above separated solution as a sample, protein expression was examined by 15% SDS-polyacrylamide gel electrophoresis. As a result, expression of the botulinum toxin-human epidermal growth factor fusion protein was confirmed from crude cell lysate in which the expression induction has been carried out with IPTG or lactose (FIG. 2A).

Figure 2B:
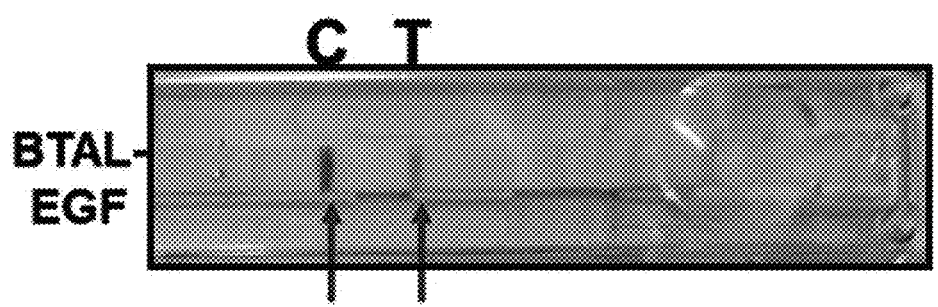

In order to determine the presence or absence of human epidermal growth factor in the botulinum toxin-human epidermal growth factor fusion protein, an EGF detection kit (manufactured by Nexgen Biotechnologies, Inc., South Korea) was used. As a result, the presence of human epidermal growth factor in the botulinum toxin-human epidermal growth factor fusion protein was confirmed (FIG. 2B).

In order to isolate and purify the botulinum toxin-human epidermal growth factor fusion protein of which expression has been confirmed from above, the inclusion body was solubilized using a solubilizing buffer solution (5M urea, pH 11), and then subjected to a refolding process using ultrafine filtration (0.45 μm fine filtration membrane, and 1K ultrafine filtration membrane). Accordingly, the botulinum toxin-human epidermal growth factor fusion protein was finally isolated by using a storage buffer solution (PBS).

Example 3. Measurement of Activity of Botulinum Toxin-Human Epidermal Growth Factor Fusion Protein—Dermal Fibroblast Proliferation Effect With selection of a sample from which the presence of isolated and purified botulinum toxin-human epidermal growth factor fusion protein has been confirmed as described in Example 2, an activity of the botulinum toxin-human epidermal growth factor fusion protein was measured.

After culturing dermal fibroblast (Human Dermal Fibroblasts adult, HDFa cell), the cells were treated with the fusion protein at concentration of 0, 0.02 ppm, or 0.2 ppm followed by culture for 3 days at 37° C. Thereafter, proliferation of the dermal fibroblast was determined based on crystal violet staining.

Figure 3:
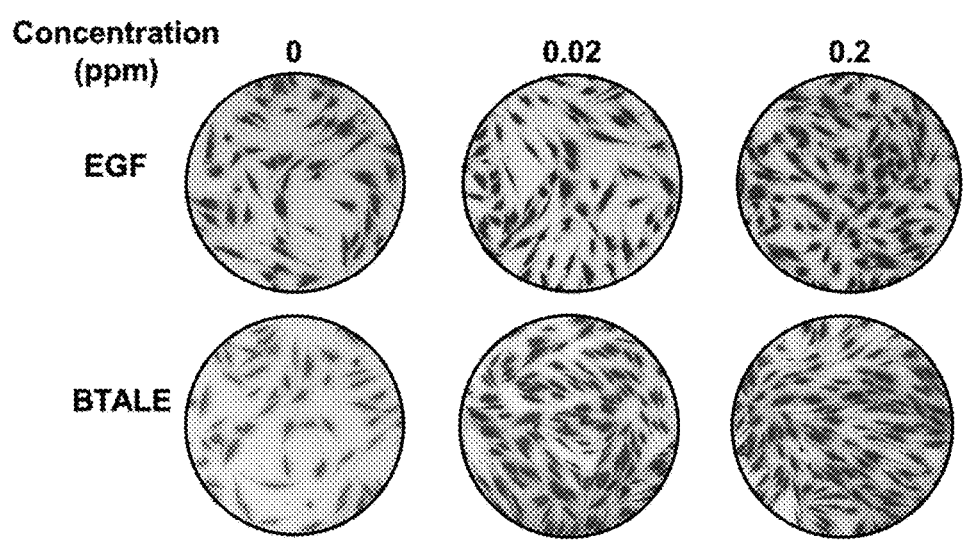
FIG. 3 is a photographic image in which the dermal fibroblast proliferation effect after the treatment of dermal fibroblast with the botulinum toxin-human epidermal growth factor fusion protein is shown by crystal violet staining.

As a result, it was found that, compared to a non-treatment control group (0 ppm), a more favorable dermal fibroblast proliferation effect is obtained as the concentration of the botulinum toxin-human epidermal growth factor fusion protein increases (0.02 to 0.2 ppm) (FIG. 3). Furthermore, compared to each of single human epidermal growth factor protein treatment group which has not been fused with any botulinum toxin protein, higher cell proliferation effect was observed with the fusion protein. Based on the above result, the synergistic effect of the botulinum toxin-human epidermal growth factor fusion protein was confirmed.

Example 4. Measurement of Anti-Oxidation Activity of Botulinum Toxin-Human Epidermal Growth Factor Fusion Protein To measure the anti-oxidation effect of the botulinum toxin-human epidermal growth factor fusion protein, DPPH (1,1-diphenyl-2-picryl hydrazyl) analysis as one of the methods for measuring free radical scavenging effect was carried out. Said reagent is present as a relatively stable free radical, and it is primarily used for test tube-based determination of a free radical scavenging activity.

Figure 4:
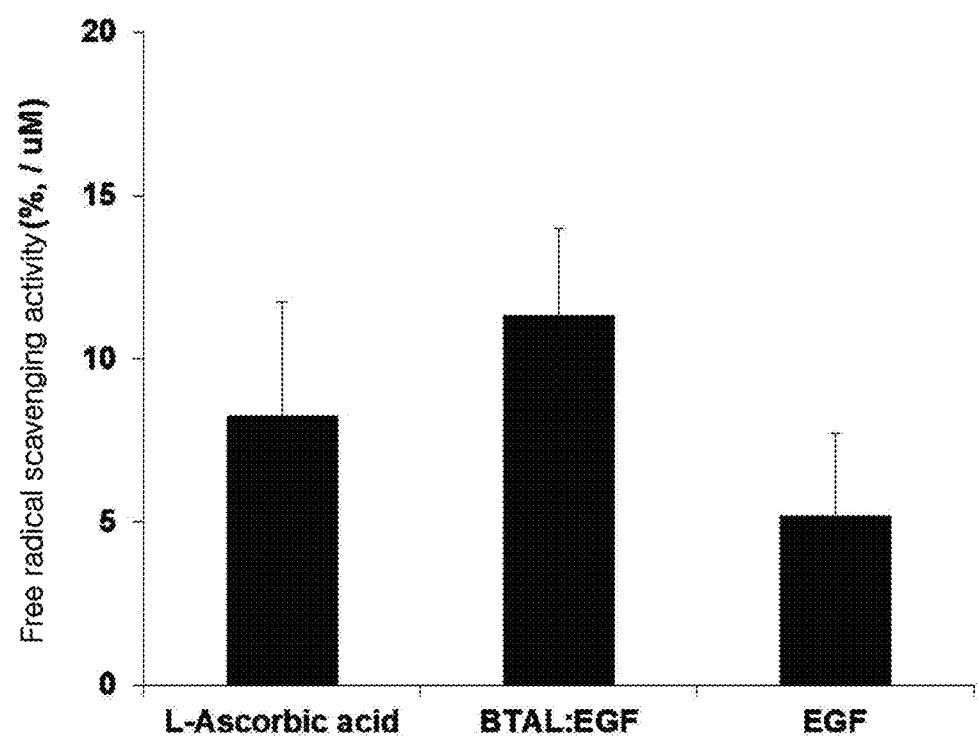
FIG. 4 shows the result illustrating the anti-oxidation effect of the botulinum toxin-human epidermal growth factor fusion protein in which the anti-oxidation effect is determined based on DPPH test.

For the DPPH analysis, L-ascorbic acid was used as a positive control. The test method is as follows. Each of L-ascorbic acid, botulinum toxin-human epidermal growth factor fusion protein, and human epidermal growth factor protein was prepared at concentration of 1 μM, and DPPH was prepared to have final concentration of 20004. After mixing each of the above proteins and DPPH at a ratio of 1:1, the mixture was allowed to stand at 37 t for 30 minutes. After that, the absorbance at 520 nm was measured by using an ELISA reader. The free radical scavenging activity (%) was calculated based on the following equation 1, and the results are shown in FIG. 4.

$$\text{Free radical scavenging activity (\%)} = 100 - ((B/A) * 100) \quad \text{(Equation 1)}$$

[A: Absorbance of control group in which the sample underwent no treatment,

B: Absorbance of test group in which the sample underwent a treatment]

As a result, the botulinum toxin-human epidermal growth factor fusion protein showed the free radical scavenging activity that is about 1.5 times higher than the L-ascorbic acid control group. Even when compared to the human epidermal growth factor protein not fused with any botulinum toxin, it showed the free radical scavenging activity that is about 2.5 times higher than that (FIG. 4). As such, it was found that the fusion protein of the present invention has even higher anti-oxidation activity due to botulinum toxin, and these results indicate that the fusion protein may have an anti-aging effect for skin based on its anti-oxidation effect.

Test Example 1. Skin Wrinkle Improvement, Skin Elasticity Maintaining Effect, and Skin Irritation Sensory Test By using the botulinum toxin-human epidermal growth factor fusion protein which has been isolated and purified as described in Example 2 as an effective component, cosmetic compositions of Preparation examples 1, 2, 3 and 4 and Comparative examples 1, 2, 3 and 4 were prepared and used for a sensory test (see, Tables 1, 3, 5 and 7).

Specifically, to confirm any wrinkle improvement, total 30 men and women with age of 30 or higher but lower than 60 (10 in 30's. 10 in 40's, and 10 in 50's and 60's) as a subject were allowed to apply, once a day for 2 weeks continuously, the composition of Comparative example (i.e., control group) around an eye area at left side of a face or around left side of lips in which many wrinkles are found, or the composition of Preparation example (i.e., test group) around an eye area at right side of a face or around right side of lips. The evaluation was made based on wrinkle reduction level around the eye or lips. Also for the skin irritation item, a sensory test was carried out according to the same method as described above in terms of itchiness, stingy feeling, and an erythema phenomenon. The evaluation was made based on five-point evaluation criteria, i.e., very excellent (5 points), excellent (4 points), moderate (3 points), poor (2 points), and very poor (1 point). Meanwhile, if the result of the sensory test cannot be described with an integer, it was described with a decimal. The results are shown in Tables 2, 4, 6, and 8.

Preparation Example 1 and Comparative Example 1

By adding the botulinum toxin-human epidermal growth factor fusion protein as an effective component and having the components and content that are described in the following Table 1, a skin of Preparation example 1 was prepared.

Furthermore, without adding the botulinum toxin-human epidermal growth factor fusion protein as an effective component but having the components and content that are described in the following Table 1, a skin of Comparative example 1 was prepared.

TABLE 1

Skin composition

| Component | Preparation example 1 (% by weight) | Comparative example 1 (% by weight) |
| --- | --- | --- |
| Botulinum toxin-human epidermal growth factor fusion protein | 0.002 | — |
| Amino acid stock | 0.1 | 0.1 |
| Mineral mixture | 0.0007 | 0.0007 |
| Purified water | q.s. | q.s. |

The sensory test results of above Preparation example 1 and Comparative example 1 are as shown in the following Table 2.

TABLE 2

Sensory test result of Preparation example 1 and Comparative example 1

Sensory test regarding wrinkle improvement effect and skin irritation

| | No. | Wrinkle improvement Preparation example | Comparative example | Skin irritation Preparation example |
|---|---|---|---|---|
| 30's | 1 | 5 | 4 | 4 |
| | 2 | 4 | 3 | 4 |
| | 3 | 4 | 5 | 4 |
| | 4 | 5 | 5 | 4 |
| | 5 | 5 | 3 | 3 |
| | 6 | 4 | 4 | 4 |
| | 7 | 5 | 3 | 4 |
| | 8 | 5 | 4 | 4 |
| | 9 | 4 | 3 | 3 |
| | 10 | 4 | 3 | 3 |
| 40's | 11 | 5 | 3 | 4 |
| | 12 | 4 | 2 | 4 |
| | 13 | 4 | 2 | 4 |
| | 14 | 4 | 3 | 4 |
| | 15 | 5 | 4 | 4.5 |
| | 16 | 5 | 3 | 4.5 |
| | 17 | 4 | 3 | 4 |
| | 18 | 5 | 3.5 | 4 |
| | 19 | 4 | 3.5 | 4 |
| | 20 | 4 | 3 | 5 |
| 50's and 60's | 21 | 4 | 3.5 | 4 |
| | 22 | 5 | 3 | 5 |
| | 23 | 4 | 3 | 4 |
| | 24 | 4.5 | 3.5 | 4 |
| | 25 | 4 | 3 | 4.5 |
| | 26 | 4 | 3 | 5 |
| | 27 | 5 | 3 | 4.5 |
| | 28 | 4 | 3 | 5 |
| | 29 | 3.5 | 3.5 | 4 |
| | 30 | 4 | 3 | 4 |
| | Average | 4.4 | 3.3 | 4.1 |

Preparation Example 2 and Comparative Example 2

By adding the botulinum toxin-human epidermal growth factor fusion protein as an effective component and having the components and content that are described in the following Table 3, an essence of Preparation example 2 was prepared.

Furthermore, without adding the botulinum toxin-human epidermal growth factor fusion protein as an effective component but having the components and content that are described in the following Table 3, an essence of Comparative example 2 was prepared.

TABLE 3

Essence composition

| Component | Preparation example 2 (% by weight) | Comparative example 2 (% by weight) |
|---|---|---|
| Botulinum toxin-human epidermal growth factor fusion protein | 0.002 | — |
| Amino acid stock | 0.05 | 0.05 |
| Mineral mixture | 0.0007 | 0.0007 |
| Glycerol | 5 | 5 |
| 1,3-Butylene glycol | 10 | 10 |
| Carbopol 940 | 0.3 | 0.3 |
| Purified water | q.s. | q.s. |

The sensory test results of above Preparation example 2 and Comparative example 2 are as shown in the following Table 4.

TABLE 4

Sensory test result of Preparation example 2 and Comparative example 2

Sensory test regarding wrinkle improvement effect and skin irritation

| | No. | Wrinkle improvement Preparation example | Comparative example | Skin irritation Preparation example |
|---|---|---|---|---|
| 30's | 1 | 5 | 4 | 4 |
| | 2 | 5 | 4 | 4 |
| | 3 | 3 | 5 | 3 |
| | 4 | 5 | 3 | 4 |
| | 5 | 5 | 3 | 3 |
| | 6 | 5 | 4 | 5 |
| | 7 | 5 | 3 | 4 |
| | 8 | 5 | 3 | 5 |
| | 9 | 4 | 3 | 3 |
| | 10 | 5 | 4 | 3 |
| 40's | 11 | 5 | 3 | 3 |
| | 12 | 5 | 3 | 4 |
| | 13 | 4 | 2 | 4 |
| | 14 | 5 | 3 | 5 |
| | 15 | 5 | 4 | 4.5 |
| | 16 | 5 | 3 | 4.5 |
| | 17 | 4 | 3 | 4 |
| | 18 | 5 | 3 | 5 |
| | 19 | 4 | 4 | 4 |
| | 20 | 4 | 3 | 5 |
| 50's and 60's | 21 | 5 | 3.5 | 4 |
| | 22 | 5 | 3 | 5 |
| | 23 | 4 | 4 | 5 |
| | 24 | 5 | 3.5 | 4 |
| | 25 | 4 | 3 | 5 |
| | 26 | 5 | 3 | 5 |
| | 27 | 5 | 3 | 4.5 |
| | 28 | 4 | 4 | 5 |
| | 29 | 3.5 | 3 | 4 |
| | 30 | 5 | 3 | 4 |
| | Average | 4.6 | 3.3 | 4.2 |

Preparation Example 3 and Comparative Example 3

By adding the botulinum toxin-human epidermal growth factor fusion protein as an effective component and having the components and content that are described in the following Table 5, a lotion of Preparation example 3 was prepared.

Furthermore, without adding the botulinum toxin-human epidermal growth factor fusion protein as an effective component but having the components and content that are described in the following Table 5, a lotion of Comparative example 3 was prepared.

TABLE 5

Lotion composition

| Component | Preparation example 3 (% by weight) | Comparative example 3 (% by weight) |
|---|---|---|
| Botulinum toxin-human epidermal growth factor fusion protein | 0.001 | — |

TABLE 5-continued

Lotion composition

| Component | Preparation example 3 (% by weight) | Comparative example 3 (% by weight) |
|---|---|---|
| Amino acid stock | 0.05 | 0.05 |
| Mineral mixture | 0.0007 | 0.0007 |
| Glycerol | 3 | 3 |
| 1,3-Butylene glycol | 10 | 10 |
| Mineral oil | 5 | 5 |
| Cetyl alcohol | 2 | 2 |
| Xanthan gum | 0.5 | 0.5 |
| Purified water | q.s. | q.s. |

The sensory test results of above Preparation example 3 and Comparative example 3 are as shown in the following Table 6.

TABLE 6

Sensory test result of Preparation example 3 and Comparative example 3

Sensory test regarding wrinkle improvement effect and skin irritation

| | | Wrinkle improvement | | |
|---|---|---|---|---|
| | No. | Preparation example | Comparative example | Skin irritation Preparation example |
| 30's | 1 | 4.5 | 3 | 5 |
| | 2 | 4 | 4 | 5 |
| | 3 | 3 | 4 | 3 |
| | 4 | 4 | 5 | 5 |
| | 5 | 4 | 3 | 5 |
| | 6 | 3 | 3 | 4 |
| | 7 | 5 | 4 | 4 |
| | 8 | 5 | 3 | 5 |
| | 9 | 5 | 3 | 4 |
| | 10 | 4 | 4 | 4 |
| 40's | 11 | 5 | 4 | 5 |
| | 12 | 5 | 3 | 4 |
| | 13 | 3 | 2 | 4 |
| | 14 | 4 | 4 | 4 |
| | 15 | 5 | 4 | 4 |
| | 16 | 4 | 3 | 4 |
| | 17 | 4 | 3.5 | 3 |
| | 18 | 4 | 3.5 | 3 |
| | 19 | 4 | 3.5 | 3 |
| | 20 | 3 | 3 | 4 |
| 50's and 60's | 21 | 3 | 3 | 4 |
| | 22 | 4 | 3.5 | 5 |
| | 23 | 4 | 3 | 4 |
| | 24 | 4 | 3.5 | 5 |
| | 25 | 3 | 3.5 | 5 |
| | 26 | 3 | 3 | 5 |
| | 27 | 4 | 3 | 5 |
| | 28 | 4 | 3 | 5 |
| | 29 | 4 | 3 | 4 |
| | 30 | 4 | 3 | 4 |
| Average | | 3.9 | 3.3 | 4.2 |

Preparation Example 4 and Comparative Example 4

By adding the botulinum toxin-human epidermal growth factor fusion protein as an effective component and having the components and content that are described in the following Table 7, a crème of Preparation example 4 was prepared.

Furthermore, without adding the botulinum toxin-human epidermal growth factor fusion protein as an effective component but having the components and content that are described in the following Table 7, a crème of Comparative example 4 was prepared.

TABLE 7

Crème composition

| Component | Preparation example 4 (% by weight) | Comparative example 4 (% by weight) |
|---|---|---|
| Botulinum toxin-human epidermal growth factor fusion protein | 0.001 | — |
| Amino acid stock | 0.05 | 0.05 |
| Mineral mixture | 0.0007 | 0.0007 |
| Glycerol | 2 | 2 |
| Mineral oil | 10 | 10 |
| Olive emulsion wax | 3 | 3 |
| Cetyl alcohol | 2 | 2 |
| Purified water | q.s. | q.s. |

The sensory test results of above Preparation example 4 and Comparative example 4 are as shown in the following Table 8.

TABLE 8

Sensory test result of Preparation example 4 and Comparative example 4

Sensory test regarding wrinkle improvement effect and skin irritation

| | | Wrinkle improvement | | |
|---|---|---|---|---|
| | No. | Preparation example | Comparative example | Skin irritation Preparation example |
| 30's | 1 | 4 | 4 | 4 |
| | 2 | 3 | 3.5 | 4 |
| | 3 | 3 | 3 | 3 |
| | 4 | 3 | 4 | 4 |
| | 5 | 3.5 | 3 | 4 |
| | 6 | 4 | 3.5 | 4 |
| | 7 | 4 | 3.5 | 4 |
| | 8 | 4 | 3.5 | 5 |
| | 9 | 4 | 4 | 5 |
| | 10 | 3.5 | 4 | 3 |
| 40's | 11 | 4 | 3.5 | 4 |
| | 12 | 4.5 | 4 | 5 |
| | 13 | 4 | 3 | 5 |
| | 14 | 3.5 | 4 | 4 |
| | 15 | 4 | 3.5 | 5 |
| | 16 | 4 | 3.5 | 4 |
| | 17 | 4 | 4 | 3 |
| | 18 | 3.5 | 3 | 3 |
| | 19 | 4 | 3 | 3 |
| | 20 | 4 | 3.5 | 4 |
| 50's and 60's | 21 | 4 | 3.5 | 5 |
| | 22 | 3.5 | 3 | 5 |
| | 23 | 5 | 4 | 4 |
| | 24 | 4 | 3.5 | 5 |
| | 25 | 4 | 3.5 | 5 |
| | 26 | 3.5 | 3 | 5 |
| | 27 | 3 | 3.5 | 4 |
| | 28 | 3 | 3 | 4 |
| | 29 | 3.5 | 3 | 4 |
| | 30 | 4 | 3 | 4 |
| Average | | 3.7 | 3.4 | 4.1 |

From the sensory test results that are given above, it was found that, when compared to Comparative examples, Preparation examples 1, 2, 3 and 4 in which the botulinum toxin-human epidermal growth factor fusion protein of the present invention is contained as an effective component have an effect of improving skin wrinkle.

The invention claimed is:

1. A botulinum toxin-human epidermal growth factor fusion protein with increased skin cell proliferation and anti-oxidation effect, the protein having the amino acid sequence of SEQ ID NO: 2.

2. A gene encoding the botulinum toxin-human epidermal growth factor fusion protein of claim 1.

3. The gene according to claim 2, wherein the gene consists of *E. coli* (*Escherichia coli*) codon-optimized nucleotide sequence of SEQ ID NO: 1.

4. A recombinant vector comprising the gene of claim 2.

5. A host cell transformed with the recombinant vector of claim 4.

6. A method for producing in a host cell a botulinum toxin-human epidermal growth factor fusion protein, the method comprising overexpressing a gene encoding a botulinum toxin-human epidermal growth factor fusion protein by transforming a host cell with the recombinant vector of claim 4.

7. The method for producing a botulinum toxin-human epidermal growth factor fusion protein according to claim 6, wherein the host cell is *E. coli*.

8. The botulinum toxin-human epidermal growth factor fusion protein produced by the method of claim 6.

9. A cosmetic composition for regenerating skin and improving skin wrinkle comprising, as an effective component, a botulinum toxin-human epidermal growth factor fusion protein with increased cell proliferation and anti-oxidation effect, the fusion protein having the amino acid sequence of SEQ ID NO: 2.

10. A recombinant vector comprising the gene of claim 3.

11. A host cell transformed with the recombinant vector of claim 10.

12. A method for producing in a host cell a botulinum toxin-human epidermal growth factor fusion protein, the method comprising overexpressing a gene encoding a botulinum toxin-human epidermal growth factor fusion protein by transforming a host cell with the recombinant vector of claim 10.

13. The method for producing the botulinum toxin-human epidermal growth factor fusion protein according to claim 12, wherein the host cell is *E. coli*.

14. The botulinum toxin-human epidermal growth factor fusion protein produced by the method of claim 12.

* * * * *